United States Patent [19]

Fiedler et al.

[11] Patent Number: 4,673,757

[45] Date of Patent: Jun. 16, 1987

[54] PROCESS FOR SELECTIVE HYDROGENATION OF C-C DOUBLE BONDS IN THE PRESENCE OF REDUCIBLE, NITROGEN-CONTAINING GROUPS AND NEW RUTHENIUM COMPLEX COMPOUNDS

[75] Inventors: Paul Fiedler, Colonge; Rudolf Braden, Odenthal; Hartmuth Buding, Dormagen, all of Fed. Rep. of Germany

[73] Assignee: Bayer Aktiengesellschaft, Leverkusen, Fed. Rep. of Germany

[21] Appl. No.: 659,591

[22] Filed: Oct. 11, 1984

[30] Foreign Application Priority Data

Oct. 13, 1983 [DE] Fed. Rep. of Germany ....... 3337294

[51] Int. Cl.[4] ................. C07C 121/16; C07C 121/20; C07C 131/02; C07C 131/00
[52] U.S. Cl. .................................. 558/431; 558/432; 558/433; 558/454; 558/459; 558/467; 564/248; 564/253; 564/268; 568/939
[58] Field of Search .............................. 260/465.1, 464; 564/253, 248, 268; 558/431, 432, 433, 454, 459, 467

[56] References Cited

U.S. PATENT DOCUMENTS

| | | | |
|---|---|---|---|
| 3,454,644 | 7/1969 | Dewhirst | 564/385 |
| 3,488,400 | 1/1970 | Candlin et al. | 585/273 |
| 3,489,786 | 1/1970 | Dewhirst | 260/465.1 |

OTHER PUBLICATIONS

Fieser et al., Reagents for Organic Synthesis, vol. 1 (1967) pp.983-986.
Fieser et al., Reagents for Organic Synthesis, vol. 8 (1980) pp. 159-160.
Bruce, et al., Aust. J. Chem., 30 (1977) pp. 1601-1604.

*Primary Examiner*—Joseph Paul Brust
*Attorney, Agent, or Firm*—Sprung, Horn, Kramer & Woods

[57] ABSTRACT

Carbon-carbon double bonds are hydrogenated selectively in a compound containing a reducible, nitrogen-containing group if the hydrogenation is carried out in the presence of a ruthenium complex catalyst. Also disclosed are new ruthenium complexes for use in such selective hydrogenation.

11 Claims, No Drawings

PROCESS FOR SELECTIVE HYDROGENATION OF C-C DOUBLE BONDS IN THE PRESENCE OF REDUCIBLE, NITROGEN-CONTAINING GROUPS AND NEW RUTHENIUM COMPLEX COMPOUNDS

The present invention relates to a new process for selective catalytic hydrogenation of C—C double bonds in compounds containing reducible, nitrogen-containing groups in the presence of ruthenium complex catalysts and new ruthenium complex compounds useful for such reduction.

It is known that C—C double bonds can be hydrogenated selectively, beside nitrogen-containing reducible groups, over solid catalysts. Palladium catalysts or platinum catalysts are used for this purpose. If the olefinic double bonds are not highly substituted, they can be hydrogenated, for example, without attack on a cyano group. Yields of up to 90% are thereby achieved (see Houben-Weyl, Methoden der Organischen Chemie (Methods of Organic Chemistry), volume IV, 1c, Reduktion (Reducton) I (1980), page 168). However, the selectivity is frequently unsatisfactory. Thus, if platinum oxide is used for the hydrogenation of 1-cyanocyclohexene, only 31% of the desired cyanocyclohexane is obtained (see M. Freifelder, Practical Catalytic Hydrogenation, (1971), page 157).

The hydrogenation of unsaturated nitriles using rhodium complexes as homogeneous catalysts is attributed to G. Wilkinson. The hetero-functional cyano group is not hydrogenated on hydrogenation with the Wilkinson complex as the catalyst. However, deactivation of the catalyst may take place with nitriles, as a result of ligand exchange (see Houben-Weyl, loc. cit., pages 57 to 60).

Since rhodium complexes of the formula $[(C_6H_5)_3P]_3Rh^IX$ are also suitable for the hydrogenation of nitriles to amines (see German Auslegeschrift No. 1,793,616, column 2, line 51), it must be expected that their selectivity is not always adequate for the hydrogenation of olefinic double bonds adjacent nitrile groups.

Although it is known that halogen-containing ruthenium complexes chiefly hydrogenate terminal olefin bonds, selective hydrogenation, in particular of inner double bonds adjacent or near nitrogen-containing functional groups, has not hitherto been described. In contrast, it is known that ruthenium complexes already attack functional groups under hydrogenation conditions from 80° C. (see Houben-Weyl, loc. cit., page 56). It is known from U.S. Pat. No. 3,454,644 that keto, formyl, nitrile and non-aromatic —C=C— and —C≡C— groups can be hydrogenated with phosphine-containing ruthenium complexes of the type $L_nMX_2$ (L=CO or tertiary phosphine, n=3 or 4, M=ruthenium or osmium and X=halogen and/or hydrogen), all the groups of this type present always being hydrogenated.

Ruthenium complexes therefore cannot be expected to have a satisfactory selectivity for the hydrogenation of C—C double bonds, in particular non-terminal double bonds, adjacent reducible nitrogen-containing functional groups.

A process has now been found for selectively catalytically hydrogenating a carbon-carbon double bond in a compound possessing a reducible nitrogen-containing group, which comprises contacting said compound with hydrogen or a source of hydrogen in the presence of a catalytically active ruthenium complex which corresponds to the formula $$RuXL_1(L_2)_2$$ 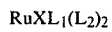

in which
X represents chlorine, bromine, iodine or hydrogen,
$L_1$ represents an aromatic ligand of the formula

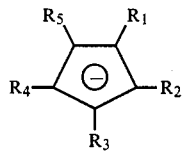

in which
$R_1$ to $R_5$ can be identical or different and represent hydrogen, methyl, ethyl or phenyl, it also being possible for in each case two adjacent radicals from the group $R_1$ to $R_5$ together to form a hydrocarbon radical such that $L_1$ overall represents a fused ring system, which optionally contains substituents which are inert under the reaction conditions, and
$L_2$ represents a ligand from the group comprising tertiary organophosphorus, organoarsene and organoantimony compounds, or $(L_2)_2$ represents a bidentate bisphosphane ligand.

In formula (I), X preferably represents hydrogen or chlorine.

Examples of $L_1$ ligands are cyclopentadienyl, pentamethylcyclopentadienyl, ethyltetramethylcyclopentadienyl, pentaphenylcyclopentadienyl and dimethyltriphenylcyclopentadienyl. Cyclopentadienyl is the preferred $L_1$ ligand.

Examples of $L_2$ ligands are those which correspond to the formulae

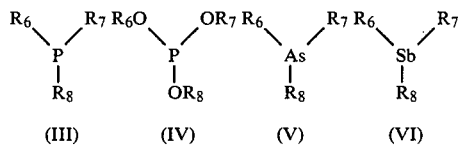

in which
$R_6$, $R_7$ and $R_8$ can be identical or different and denote alkyl, cycloalkyl, aryl or aralkyl radicals, it being possible for these radicals to be optionally substituted by alkyl, hydroxyl, alkoxy, carbalkoxy or halogen groups.

Examples of alkyl radicals here are straight-chain or branched, saturated hydrocarbon radicals with 1 to 20, preferably 1 to 12 and particularly preferably 1 to 6, C atoms. Particularly preferred alkyl radicals are, for example, methyl, ethyl, propyl, isopropyl, butyl, isobutyl, pentyl, isopentyl, hexyl and isohexyl.

Examples of cycloalkyl radicals here are cyclic, saturated hydrocarbon radicals with 5 to 12, preferably 5 to 7, C atoms, such as cyclopentyl, cyclohexyl and cycloheptyl.

Examples of aryl radicals here are aromatic hydrocarbon radicals from the benzene series with 6 to 18, preferably 6 to 12, C atoms, for example phenyl, biphenyl, naphthyl and anthracyl.

Examples of aralkyl radicals here are alkyl radicals which are substituted by aryl and which consist, in the aliphatic part, of a straight-chain or branched hydrocarbon radical with 1 to 6 C atoms and, in the aromatic part, of a radical of the benzene series, preferably phenyl. An example here is the benzyl radical.

The alkyl, cycloalkyl, aryl and aralkyl radicals described above can optionally be substituted by $C_1$- to $C_6$-alkyl, hydroxyl, $C_1$- to $C_6$-alkoxy, $C_1$- to $C_6$-carbalkoxy, fluorine or chlorine. Examples of alkyl substituents are methyl, ethyl, propyl, isopropyl, butyl, isobutyl, pentyl, isopentyl, hexyl and isohexyl.

Examples of alkoxy substituents are methoxy, ethoxy, propoxy, isopropoxy, butoxy, isobutoxy, pentoxy, isopentoxy, hexoxy and isohexoxy. Examples of carbalkoxy substituents are carbmethoxy, carbethoxy, carbisopropoxy and carbpropoxy. Of the substituents fluorine and chlorine, fluorine is preferred.

Preferred $L_2$ ligands are those of the formula (III). Examples of these are triphenylphosphane, diethylphenylphosphane, tritolylphosphane, trinaphthylphosphane, diphenylmethylphosphane, diphenylbutylphosphane, tris-(p-carbmethoxyphenyl)-phosphane, tris-(p-cyanophenyl)-phosphane, tributylphosphane, tris-(trimethylphenyl)-phosphanes, tris-(trimethoxyphenyl)-phosphanes, bis-(trimethylphenyl)-phenylphosphanes, bis-(trimethoxyphenyl)-phenylphosphanes, trimethylphenyl-diphenylphosphanes, trimethoxyphenyldiphenylphosphanes, tris-(dimethylphenyl)-phenylphosphanes, tris-(dimethoxyphenyl)-phosphanes, bis-(dimethylphenyl)-phenylphosphanes, bis-(dimethoxyphenyl)-phenylphosphanes, dimethylphenyldiphenylphosphanes and dimethoxyphenyldiphenylphosphanes.

If the group $(L_2)_2$ in the formula (I) represents a bidentate bisphosphane ligand, this can correspond, for example, to the formula

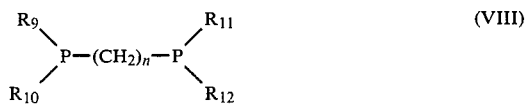

in which
n represents an integer from 1 to 10 and the radicals $R_9$, $R_{10}$, $R_{11}$ and $R_{12}$ can be identical or different and correspond in meaning to the radicals $R_6$, $R_7$ and $R_8$ as described for formulae (III) to (VI).

Examples of bisphosphanes of this group are 1,2-bis-dianisylphosphanoethane and 1,4-bis-diphenylphosphanobutane.

Some of the ruthenium complexes of the formula $$RuXL_1(L_2)_2 \qquad (I)$$

in which
$L_1$ denotes cyclopentadienyl,
$L_2$ denotes simple phosphanes or phosphites, such as triphenylphosphane, tritolylphosphane or trimethyl phosphite, and
X represents chlorine, bromine, iodine or hydrogen, are known (see M. I. Bruce, N. J. Windsor, Aust. J. Chem. 30 (1977), pages 1601 to 1604).

The ruthenium complexes of the formula

in which
X is hydrogen,
can be obtained, for example, by hydrogenation of the corresponding ruthenium complexes of the formula (I) in which X is chlorine. This hydrogenation can be carried out, for example, by reaction with lithium alanate in ether (see T. Blackmore, M. I. Bruce and F. G. A. Stoue, J. Chem. Soc. Sect. A 1971, pages 2376 to 2382), or by reaction with sodium methylate in methanol (see T. Wilczewsky, M. Bochenska and J. F. Biernat, J. Organomet. Chem. 215 (1981), pages 87 to 96).

The ruthenium complexes of the formula

in which
X is chlorine,
can be obtained, for example, by reaction of hydrated ruthenium trichloride with an excess of the ligands $L_1$ and $L_2$ in ethanol (see. M. I. Bruce and N. J. Windsor, Aust. J. Chem. 30 (1977), pages 1601 to 1604).

The ruthenium complexes of the formula

in which
X is bromine or iodine,
can be obtained, for example, simply by heating the corresponding ruthenium complexes of the formula (I) in which X is hydrogen with HBr or HI in methanol (see T. Wilczewsky, M. Bochenska, J. F. Biernat in J. Organomet. Chem. 215, pages 87 to 96).

For carrying out the process according to the invention, for example, 0.001 to 50 mmol of a catalytically active ruthenium complex of the type described above can be employed per mol of C—C double bond to be hydrogenated. Catalyst amounts of 0.01 to 10 mmol per mol of C—C double bond to be hydrogenated are preferably used. The process according to the invention is in general carried out in the temperature range from 20° to 250° C. Temperatures in the range from 80° to 150° C. are preferred.

The process according to the invention is in general carried out in the pressure range from 5 to 300 bar. Pressures below 5 bar are also possible, in which case, however, the reaction time usually has to be increased. The process according to the invention can likewise be carried out under higher pressures than 300 bar, but this is associated with an increased technical effort. The process according to the invention is preferably carried out in the pressure range between 20 and 200 bar.

Compounds of the formulae (III), (IV), (V) and (VI) are preferably introduced into the process according to the invention only in the form of the ruthenium complexes of the formula (I) or (VII), that is to say not in the free form.

The process according to the invention is in general carried out in the liquid phase. The liquid reaction mixture can be a mixture of liquids which are present per se, that is to say a mixture of the starting materials and reaction products, or, in particular, if the starting materials and/or reaction products are solid under the reaction conditions, can consist of an added solvent, which is inert under the reaction conditions.

If the process according to the invention is to be carried out in the presence of a solvent, it is possible to add, for example, organic solvents which do not change under the reaction conditions. Possible examples of these are halogen-, alkyl- or alkoxy-substituted benzenes, such as chlorobenzene, toluene, xylenes and anisole; esters, such as ethyl acetate or dimethyl adipate; esters and ethers of polyols, such as glycol diacetate or tetraglyme; cyclic ethers, such as tetrahydrofuran and dioxane; lower alcohols, such as methanol and isopropanol; or ketones, such as acetone, butanone, diisopropyl ketone and cyclohexanone. Preferred solvents are toluene, isopropanol and butanone.

The solvents can be used in a weight ratio of, for example, 30:1 to 1:10, based on the starting substance. This ratio is preferably 15:1 to 1:3.

The most diverse compounds containing C—C double bonds are reducible nitrogen-containing groups can be selectively hydrogenated on the C—C double bonds by the process according to the invention. Examples of reducible nitrogen-containing groups which can be present are nitrile groups, and also oximine and/or imine groups. Several reducible nitrogen-containing groups, including different groups, may be present. The C—C double bonds can be olefinic double bonds, which can be in open-chain compounds in inner or terminal positions or in cyclic compounds. Examples of compounds which can be selectively hydrogenated in the manner according to the invention are alkene-nitriles, alkene-dinitriles, alkene-carbaldoximes, alkenecarbaldimines, in each case preferably containing 2 to 20 C atoms, and cycloalkene-nitriles, cycloalkene-carbaldoximes, cycloalkene-carbaldimines and nitroarylalkenes, in each case preferably containing 5 to 12 C atoms.

The starting material can furthermore optionally contain keto, carboxyl, carboxylic acid ester and/or carboxamide groups.

The yields and selectivities which can be achieved with the process according to the invention are very high. In general, the yields are between 90 and 100% and the selectivities are between 95 and 100%.

Since the process according to the invention is in general carried out under a hydrogen pressure, the course of the reaction can easily be observed by the drop in pressure. The end of the reaction can be recognised by a stationary pressure. The high selectivity is retained even if the reaction time is further increased. Examples of customary reaction times are 30 minutes to 10 hours; however, both shorter and longer reaction times may arise, depending on the catalyst, catalyst concentration and substrate.

The present invention furthermore relates to new ruthenium complex compounds of the formula

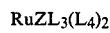

in which
Z represents chlorine, bromine, iodine or hydrogen,
L₃ represents an optionally substituted cyclopentadienyl ligand and
L₄ represents a triorganophosphane ligand, with the proviso that L₃ only represents an unsubstituted cyclopentadienyl ligand if L₄ represents a triarylphosphane ligand containing at least one phenyl ring carrying at least one inert substituent which is not methyl, or
(L₄)₂ represents a bidentate bisphosphane ligand of the type Ph₂P—(CH₂)ₙ—PPh₂, whereby n represents an integer from 1 to 10 and Ph represents an optionally substituted phenyl radical, with the proviso that L₃ only represents an unsubstituted cyclopentadienyl ligand if the biphosphane ligand is not (C₆H₅)₂P—(CH₂)₂—P(C₆H₅).

The ligand L₄ can be, for example, a triorganophosphane ligand of the formula

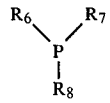

in which
R₆, R₇ and R₈ can be identical or different and denote alkyl, cycloalkyl, aryl or aralkyl radicals, it being possible for these radicals optionally to carry inert substituents, such as alkyl, hydroxyl, alkoxy, carbalkoxy or halogen.

Examples of these are triphenylphosphane, diethylphenylphosphane, tritolylphosphane, trinaphthylphosphane, diphenylmethylphosphane, diphenylbutylphosphane, tris-(p-carbmethoxyphenyl)-phosphane, tris-(p-cyanophenyl)-phosphane, tributylphosphane, tris-(trimethylphenyl)-phosphanes, tris-(trimethoxyphenyl)-phosphanes, bis-(trimethylphenyl)-phenylphosphanes, bis-(trimethoxyphenyl)-phenylphosphanes, trimethylphenyl-diphenylphosphanes, trimethoxyphenyldiphenylphosphanes, tris-(dimethylphenyl)-phenylphosphanes, tris-(dimethoxyphenyl)-phosphanes, bis-(dimethylphenyl)-phenylphosphanes, bis-(dimethoxyphenyl)-phenylphosphanes, dimethylphenyldiphenylphosphanes and dimethoxyphenyldiphenylphosphanes.

The new ruthenium complex compounds of the formula $$RuZL_3(L_4)_2 \quad (VII)$$

can be obtained, for example, by reacting hydrated ruthenium trichloride with an excess of the ligands L₃ and L₄ in ethanol, or by reacting RuClL₃(PPh₃)₂ with an excess of a ligand L₄ in ethanol.

To avoid long reaction times, it can be advantageous to run these reactions at elevated reaction temperatures in the presence of solvents, such as higher alcohols, for example butanol or hexanol.

The new ruthenium complexes according to the invention are in general obtained in yields of up to 90%, and in some cases even more.

It was not to be expected that the new ruthenium complexes of the formula (VII) in which sterically hindered ligands are present can be prepared in a similarly simple manner to ruthenium complexes with simple ligands.

The use of the new ruthenium complex compounds of the formula $$RuZL_3(L_4)_2 \quad (VII)$$

for selective hydrogenation of C—C double bonds has likewise already been described above.

The following examples illustrate the present invention, without in any way limiting it.

EXAMPLES

EXAMPLES 1 TO 9

A 15% strength solution of the educt in butanone and 0.03 mol % of the catalyst were initially introduced into a stirred stainless steel autoclave with a capacity of 0.3 liter, the autoclave was closed and the mixture was heated to the given temperature, under a hydrogen pressure. The pressure was kept at the given value by regular subsequent forcing in of hydrogen. As soon as no further drop in pressure occurred, the mixture was cooled and let down. The reaction solution was investigated by gas chromatography and worked up by distillation, the product isolated being investigated by spectroscopy (IR and NMR) for any hydrogenated nitrogen-containing groups present.

The starting materials, reaction conditions and results were as follows, Cp representing cyclopentadienyl, Ph representing phenyl, MeO representing methoxy and Me representing methyl, and selectively meaning the yield of the stated product, based on the conversion.

EXAMPLE 1

Educt: cyclohex-3-ene-nitrile, product: cyclohexane-nitrile, catalyst: RuCl(Cp)(PPh$_3$)$_2$, reaction temperature: 120° C., reaction pressure: 130 bar, conversion: 100%, selectivity: 100%.

EXAMPLE 2

Educt: cyclohex-3-ene-nitrile, product: cyclohexane-nitrile, catalyst: RuH(Cp)(PPh$_3$)$_2$, reaction temperature: 120° C., reaction pressure: 140 bar, conversion: 100%, selectivity: 100%.

EXAMPLE 3

Educt: cyclohex-3-ene-carbaldoxime, product: cyclohexane-carbaldoxime, catalyst: RuCl(Cp)(PPh$_3$)$_2$, reaction temperature: 120° C., reaction pressure: 140 bar, conversion: 90%, selectivity: 100%.

EXAMPLE 4

Educt: cyclohex-3-ene-nitrile, product: cyclohexane-nitrile, catalyst: RuCl(1,2,4-Ph$_3$C$_5$Me$_2$)(PPh$_3$)$_2$, reaction temperature: 120° C., reaction pressure: 120 bar, conversion: 100%, selectivity: 100%.

EXAMPLE 5

Educt: acrylonitrile, product: propionitrile, catalyst: RuH(Cp)[(4-MeO-C$_6$H$_4$)$_3$P]$_2$, reaction temperature: 120° C., reaction pressure: 130 bar, conversion: 100%, selectivity: 100%.

EXAMPLE 6

Educt: cyclohex-3-ene-N-phenylcarbaldimine, product: cyclohexane-N-phenylcarbaldimine, catalyst: RuCl(Cp)(PPh$_3$)$_2$, reaction temperature: 120° C., reaction pressure: 130 bar, conversion: 90%, selectivity: 98%.

EXAMPLE 7

Educt: cyclohex-3-ene-nitrile, product: cyclohexane-nitrile, catalyst RuCl(Cp)(PPh$_3$)$_2$, reaction temperature: 170° C., reaction pressure: 150 bar, conversion: 100%, selectivity: 100%.

EXAMPLE 8

Educt: cyclohex-3-ene-nitrile, product: cyclohexane-nitrile, catalyst: RuCl(Cp)[(2-Me-C$_6$H$_4$)$_3$P$_2$, reaction temperature: 120° C., reaction pressure: 130 bar, conversion: 100%, selectivity: 100%.

EXAMPLE 9

Educt: cyclohex-3-ene-nitrile, product: cyclohexane-nitrile, catalyst: RuCl(Cp)[(2,4,6-Me$_2$C$_6$H$_2$)$_3$P]$_2$, reaction temperature: 120° C., reaction temperature: 120 bar, conversion: 100%, selectivity: 100%.

EXAMPLES 10 TO 18

All the experiments were carried out under a protective gas atmosphere (argon or nitrogen).

EXAMPLE 10

Preparation of RuCl(Me$_5$C$_5$)(PPh$_3$)$_2$ 4.0 g of triphenylphosphane were dissolved in 100 ml of boiling ethanol in a glass flask, and 1.0 g of RuCl$_3$.3-H$_2$O, dissolved in 30 ml of ethanol, and 5.0 g of pentamethylcyclopentadiene, dissolved in 20 ml of ethanol, were rapidly added in succession. The mixture was boiled under reflux for a further 6 hours and allowed to cool slowly (0° C.) and the crystals precipitated were filtered off with suction. These were washed with water, ethanol, ether and hexane and dried in vacuo.

Yield: 1.2 g, melting point: 152°–154° C.

IR (cm$^{-1}$): 3060, 1590, 1570, 1480, 1435, 1190, 1120, 1090, 740, 695 and 520.

EXAMPLE 11

Preparation of RuCl(Cp)[(4-MeO-C$_6$H$_4$)$_3$P]$_2$ 5.4 g of (4-MeOC$_6$H$_4$)$_3$P were dissolved in boiling ethanol in a glass flask and 1.0 g of RuCl$_3$.3H$_2$O, dissolved in 30 ml of ethanol, and 8.0 g of cyclopentadiene, dissolved in 20 ml of ethanol, were rapidly added in succession. The mixture was boiled under reflux for a further 4 hours and allowed to cool slowly (5° C.) and the crystals precipitated were filtered off with suction. These were washed with water, ethanol, ether and hexane and dried in vacuo.

Yield: 1.0 g, melting point: 190° C.

IR (cm$^{-1}$): 3040, 1595, 1570, 1500, 1290, 1260, 1180, 1120, 1025, 830, 800 and 540.

EXAMPLE 12

Preparation of RuCl(Cp)(Ph$_2$PC$_2$H$_5$)$_2$ 3.5 g of Ph$_2$PC$_2$H$_5$ were dissolved in 100 ml of boiling ethanol in a glass flask and 1.0 g of RuCl.3H$_2$O, dissolved in 30 ml of ethanol, and 8.0 g of cyclopentadiene, dissolved in 20 ml of ethanol, were rapidly added in succession. The mixture was boiled under reflux for a further 1 hour and allowed to cool slowly (0° C.) and the crystals precipitated were filtered off with suction. These were washed with water, ethanol, ether and hexane and dried in vacuo.

Yield: 1.5 g, melting point: 182°–188° C.

IR (cm$^{-1}$): 3050, 1590, 1570, 1480, 1435, 1085, 1000, 935, 910, 850, 840, 695,530, 520 and 500.

EXAMPLE 13

Preparation of RuCl(Cp)[Ph$_2$P(CH$_2$)$_4$PPh$_2$ 4.8 g of Ph$_2$P(CH$_2$)$_4$PPh$_2$ were dissolved in 100 ml of boiling ethanol in a glass flask and 1 g of RuCl$_3$.3H$_2$O, dissolved in 30 ml of ethanol, and 8.0 g of cyclopentadiene, dissolved in 20 ml of ethanol, were rapidly added in succession. The mixture was boiled under reflux for a further 2 hours and allowed to cool slowly (5° C.) and the crystals precipitated were filtered off with suction. These were washed with water, ethanol, ether and hexane and dried in vacuo.

Yield: 0.4 g, melting point: >220° C.

IR (cm$^{-1}$): 3060, 1590, 1570, 1480, 1435, 1120, 1090, 1000, 880, 745, 725, 695, 540 and 520.

EXAMPLE 14

Preparation of RuCl(Cp)[(2,4,6-Me$_3$C$_6$H$_2$)$_3$P]$_2$ 7.1 g of (2,4,6-Me₃C₆H₂)₃P were dissolved in 100 ml of boiling ethanol in a glass flask and 1.0 g of RuCl₃.3H₂O, dissolved in 30 ml of ethanol, and 8.0 g of cyclopentadiene, dissolved in 20 ml of ethanol, were rapidly added in succession. The mixture was boiled under reflux for a further 6 hours and allowed to cool slowly (0° C.) and the crystals precipitated were filtered off with suction. These were washed with water, ethanol, ether and hexane and dried in vacuo.

Yield: 0.7 g, melting point: >230° C.

IR (cm⁻¹): 3080, 1700, 1585, 1520, 1430, 1410, 1325, 1290, 1170, 1140, 1100, 1065, 1020, 865, 810, 780, 705 and 540.

EXAMPLE 15

Preparation of RuCl(Ph₅C₅)(PPh₃)₂

4.0 g of triphenylphosphane were dissolved in 100 ml of boiling ethanol in a glass flask and 1.0 g of RuCl₃.3H₂O, dissolved in 30 ml of ethanol, and 5.0 g of pentaphenylcyclopentadiene, dissolved in 30 ml of ethanol, were rapidly added in succession. The mixture was boiled under reflux for a further 4 hours and allowed to cool slowly (5° C.) and the crystals precipitated were filtered off with suction. These were washed with water, ethanol, ether and hexane and dried in vacuo.

Yield: 2.8 g, melting point: 230° C. (decomposition)

IR (cm⁻¹): 3060, 1590, 1570, 1480, 1430, 1190, 1090, 1000, 745, 695, 550 and 520.

EXAMPLE 16

Preparation of RuCl(2,4-dimethyltriphenylcyclopentadienyl)(PPh₃)₂

4.0 g of triphenylphosphane were dissolved in 100 ml of boiling ethanol in a glass flask and 1.0 g of RuCl₃.3H₂O, dissolved in 30 ml of ethanol, and 2.3 g of 2,4-dimethyltriphenylcyclopentadiene, dissolved in 30 ml of ethanol, were rapidly added in succession. The mixture was boiled under reflux for a further 4 hours and allowed to cool slowly (5° C.) and the crystals precipitated were filtered off with suction. These were washed with water, ethanol, ether and hexane and dried in vacuo.

Yield: 2.8 g, melting point: 196°–198° C.

IR (cm⁻¹): 3060, 1590, 1570, 1480, 1435, 1190, 1090, 1000, 740, 695, 540 and 520.

EXAMPLE 17

Preparation of RuCl(Cp)[(4-Me₂NC₆H₄)₃P]₂

6.0 of (Me₂NC₆H₄)₃P were dissolved in 100 ml of boiling ethanol in a glass flask and 1.0 g of RuCl₃.3H₂O, dissolved in 30 ml of ethanol, and 6 g of cyclopentadiene, dissolved in 20 ml of ethanol, were rapidly added in succession. The mixture was boiled under reflux for a further 4 hours and allowed to cool slowly (5° C.) and the crystals precipitated were filtered off with suction. These were washed with water, ethanol, ether and hexane and dried in vacuo.

Yield: 1.1 g, melting point: >230° C.

IR (cm⁻¹): 3040, 2890, 2810, 1600, 1550, 1520, 1450, 1340, 1290, 1230, 1205, 1165, 1120, 945, 820, 650, 630, 540 and 505.

EXAMPLE 18

Preparation of RuH(Cp)[(4-MeOC₆H₄)₃P]₂

0.3 g of sodium was dissolved in 100 ml of methanol, 1 g of RuCl(Cp)[(4-MeOC₆H₄)₃P]₂ was added and the suspension formed was stirred at room temperature for 1 hour. The mixture was stirred at 50° C. for a further 30 minutes and cooled with ice and the crystals were filtered off with suction and washed with ether and hexane.

Yield: 0.9 g, melting point: >230° C.

IR (cm⁻¹): 3060, 1935, 1580, 1480, 1280, 1240, 1160, 1100, 1010, 810 and 780.

What is claimed is:

1. A process for selectively catalytically hydrogenating a carbon-carbon double bond in a compound possessing a reducible nitrogen-containing group which comprises contacting said compound in liquid phase with hydrogen in the presence of a catalytically active ruthenium complex which corresponds to the formula $$RuXL_1(L_2)_2$$

in which

X represents chlorine, bromine, iodine or hydrogen,

L₁ represents an aromatic ligand of the formula

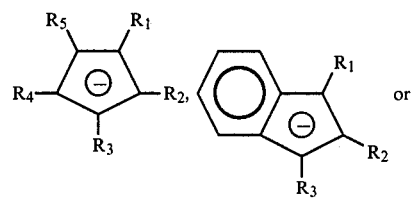

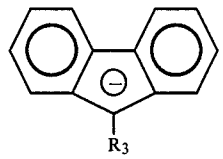

in which

R₁ to R₅ can be identical or different and represent hydrogen, methyl, ethyl or phenyl and L₂ represents a ligand of the formula

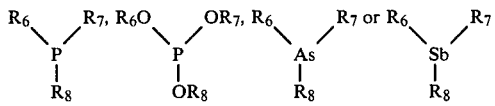

in which

R₆, R₇ and R₈ can be identical or different and denote alkyl, cycloakyl or alkyl or cycloalkyl substituted by hydroxyl, alkoxy, carbalkoxy or halogen groups or aryl, aralkyl or aryl or aralkyl substituted by alkyl, hydroxyl, alkoxy, carbalkoxy or halogen groups or (L₂)₂ represents a bidentate bisphosphane ligand of the formula

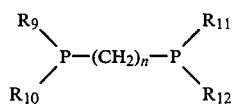

in which n represents an integer from 1 to 10 and the radicals R₉, R₁₀, R₁₁ and R₁₂ can be identical or different and denote alkyl, cycloalkyl or alkyl or cycloalkyl substituted by hydroxy, alkoxy, carbalkoxy or halogen groups or aryl, aralkyl or aryl or aralkyl substituted by alkyl, hydroxyl, alkoxy, carbalkoxy or halogen groups wherein the compound to be catalytically selectively hydrogenated is selected in the group consisting of alkene-nitriles having 2 to 20 carbon atoms in the alkene portion, alkene-dinitriles having 2 to 20 carbon atoms in the alkene portion, alkene-carbaldoximes having 2 to 20 carbon atoms in the alkene portion, cycloalkene-nitriles having 5 to 12 carbon atoms in the cycloalkene portion, cycloalkene-carbaldoximes having 5 to 12 carbon atoms in the cycloalkene portion, cycloalkene-carbaldimines having 5 to 12 carbon atoms in the the cycloalkene portion and nitroarylalkenes of of 5 to 12 carbon atoms.

2. A process according to claim 1 wherein $L_1$ represents cyclopentadienyl, pentamethylcyclopentadienyl, ethyltetramethylcyclopentadienyl, pentaphenylcyclopentadienyl or dimethyltriphenylcyclopentadienyl.

3. A process according to claim 1 wherein $L_1$ represents cyclopentadienyl.

4. A process according to claim 1 wherein $L_2$ represents a ligand of the formula

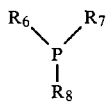

5. A process according to claim 1 wherein the catalytically active ruthenium complex is employed in an amount of 0.001 to 50 mmol per mol of C—C double bond to be hydrogenated.

6. A process according to claim 1 wherein the process is carried out at 20° to 250° C.

7. A process according to claim 1 wherein the process is carried out under a hydrogen gas pressure of 5 to 300 bar.

8. A process according to claim 1 wherein the process is carried out in the presence of a solvent which is used in a weight ratio of 30:1 to 1:10, based on the weight of the compound to be selectively catalytically hydrogenated.

9. A process according to claim 1 wherein said compound to be selectively hydrogenated is selected from the group consisting of cyclohex-3-ene-nitrile, cyclohex-3-ene-carbaldoxime, acrylonitrile and cyclohex-3-ene-N-phenylcarbaldimine.

10. A process according to claim 1 wherein said ruthenium catalyst is one wherein:
$L_1$ denotes cyclopentadienyl,
$L_2$ denotes a a ligand of the formula

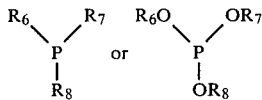

and

X represents chlorine, bromine, iodine or hydrogen.

11. A process according to claim 1 wherein said ruthenium catalyst is one in which
$L_1$ represents unsubstituted or substituted cyclopentadienyl ligand and
$L_2$ represents a ligand of the formula

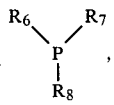

with the proviso that $L_1$ only represents an unsubstituted cyclopentadienyl ligand if $L_2$ represents a triarylphosphane ligand containing at least one phenyl ring carrying at least one inert substituent which is not methyl, or $(L_2)_2$ represents a bidentate phosphane ligand of the type $Ph_2P-(CH_2)_n-PPh_2$, whereby n represents an integer from 1 to 10 and Ph represents an optionally substituted phenyl radical, with the proviso that $L_1$ only represents an unsubstituted cyclopentadienyl ligand if the bisphosphane ligand is not $(C_6H_5)_2P-(CH_2)_2-P(C_6H_5)_2$.

* * * * *

UNITED STATES PATENT AND TRADEMARK OFFICE
CERTIFICATE OF CORRECTION

PATENT NO. : 4,673,757

DATED : June 16, 1987

INVENTOR(S) : Paul Fiedler, et al.

It is certified that error appears in the above-identified patent and that said Letters Patent is hereby corrected as shown below:

Col. 3, line 58 and Col. 4, line 15 — Delete "30" and substitute --$\underline{30}$--

Col. 4, line 26 — Delete "215" and substitute --$\underline{215}$--

Col. 5, line 66 — Delete "$P(C_6H_5)$" and substitute --$P(C_6H_5)_2$--

Col. 8, line 49 — After "695," insert space

Signed and Sealed this

Third Day of May, 1988

Attest:

DONALD J. QUIGG

Attesting Officer   Commissioner of Patents and Trademarks